(12) United States Patent
Davis et al.

(10) Patent No.: US 9,409,841 B2
(45) Date of Patent: Aug. 9, 2016

(54) PROCESS AND APPARATUS FOR MAKING PHENOL AND/OR CYCLOHEXANONE

(71) Applicant: ExxonMobil Chemical Patents Inc., Baytown, TX (US)

(72) Inventors: Jason D. Davis, Beaumont, TX (US); Christopher L. Becker, Manhattan, KS (US); Bryan A. Patel, Jersey City, NJ (US); John S. Coleman, Houston, TX (US); Hari Nair, Somerville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/779,131

(22) PCT Filed: Mar. 24, 2014

(86) PCT No.: PCT/US2014/031535
§ 371 (c)(1),
(2) Date: Sep. 22, 2015

(87) PCT Pub. No.: WO2014/165339
PCT Pub. Date: Oct. 9, 2014

(65) Prior Publication Data
US 2016/0046550 A1    Feb. 18, 2016

Related U.S. Application Data

(60) Provisional application No. 61/807,407, filed on Apr. 2, 2013.

(30) Foreign Application Priority Data

Jun. 25, 2013  (EP) ...................................... 1373544

(51) Int. Cl.
| | |
|---|---|
| *C07C 45/53* | (2006.01) |
| *C07C 37/08* | (2006.01) |
| *C07C 2/74* | (2006.01) |
| *B01J 19/00* | (2006.01) |
| *C07C 407/00* | (2006.01) |
| *B01J 19/24* | (2006.01) |

(52) U.S. Cl.
CPC ............... *C07C 37/08* (2013.01); *B01J 19/245* (2013.01); *C07C 45/53* (2013.01); *C07C 407/00* (2013.01); *B01J 2219/00103* (2013.01); *B01J 2219/24* (2013.01); *C07C 2101/14* (2013.01)

(58) Field of Classification Search
CPC .......... C07C 45/53; C07C 37/08; C07C 2/74; B01J 2219/24; B01J 2219/0013
USPC ............ 568/342, 798; 585/467; 422/187, 649
See application file for complete search history.

(56) References Cited

U.S. PATENT DOCUMENTS

| 6,303,825 | B1 | 10/2001 | Gerlich et al. |
|---|---|---|---|
| 7,312,365 | B2 | 12/2007 | Black |

FOREIGN PATENT DOCUMENTS

| EP | 0 492 807 | 7/1992 |
|---|---|---|
| WO | 2009/128984 | 10/2009 |
| WO | 2009/131769 | 10/2009 |
| WO | 2011/100013 | 8/2011 |
| WO | 2012/036822 | 3/2012 |
| WO | 2013/165656 | 11/2013 |
| WO | 2013/165659 | 11/2013 |

OTHER PUBLICATIONS

Middleton et al., "Loop Reactors", Ullmann's Encyclopedia of Industrial Chemistry, vol. 21, (2010), pp. 377-382.

*Primary Examiner* — Sikarl Witherspoon
(74) *Attorney, Agent, or Firm* — Stephen A. Baehl

(57) ABSTRACT

A process for producing phenol and/or cyclohexanone by cleaving cyclohexylbenzene hydroperoxide in a loop cleavage reactor comprising multiple reaction zones connected in series. In desirable embodiments, fresh cyclohexylbenzene hydroperoxide feed(s) are supplied to reaction zones the final reaction zone, and fresh acid catalyst is supplied only to the final reaction zone. In desirable embodiments, a portion of the effluent exiting the final reaction zone is recycled to the first reaction zone. Each reaction zone is equipped with a heat exchanger downstream of the feed port to extract heat generated from the cleavage reaction.

25 Claims, 1 Drawing Sheet

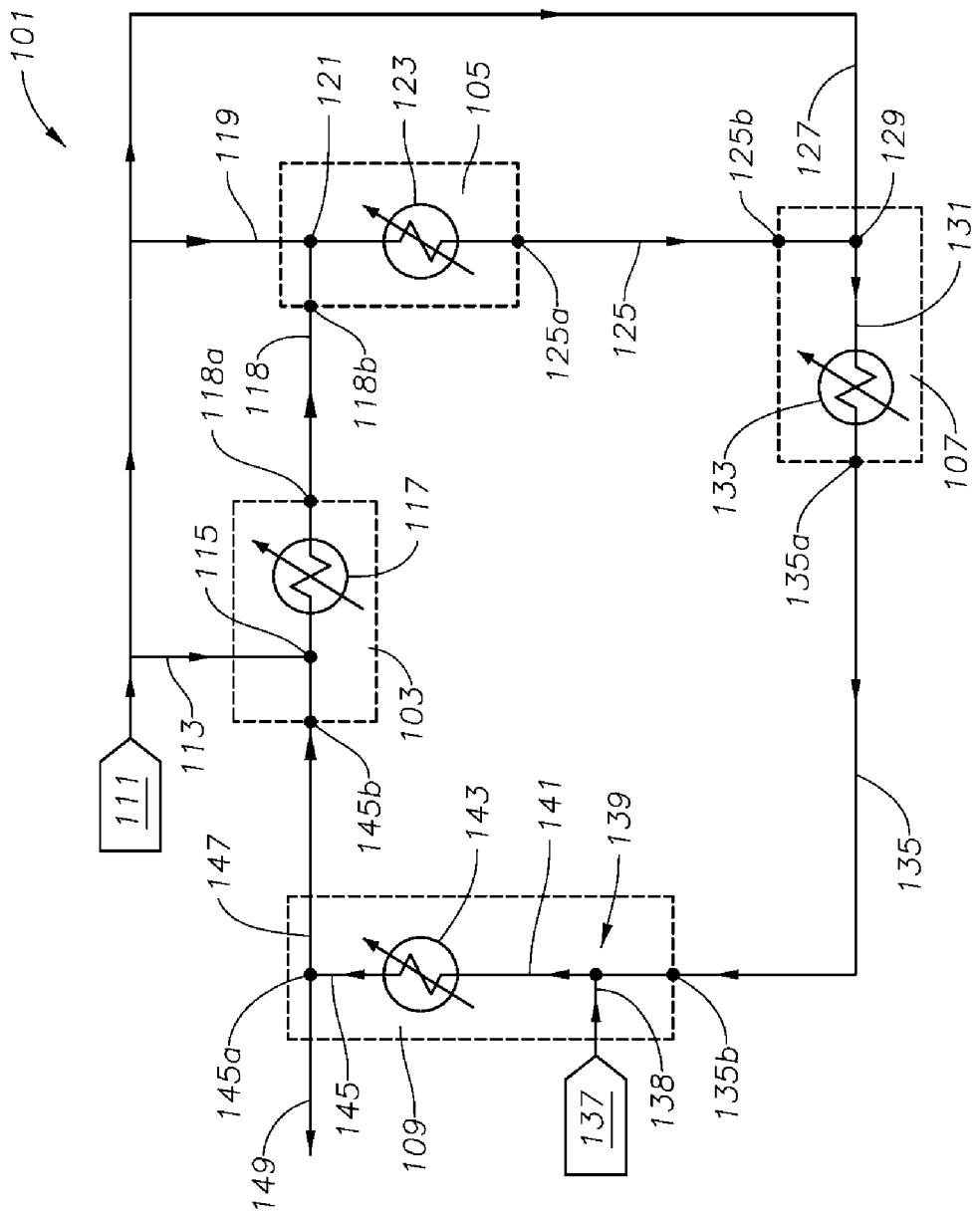

PROCESS AND APPARATUS FOR MAKING PHENOL AND/OR CYCLOHEXANONE

CROSS-REFERENCE OF RELATED APPLICATIONS

This application is a National Stage Application of International Application No. PCT/US2014/031535 filed Mar. 24, 2014, which claims the benefit of Ser. No. 61/807,407 filed Apr. 2, 2013 and European Application No. 13173544.1 filed Jun. 25, 2013, the disclosures of which are incorporated by reference in their entireties.

TECHNICAL FIELD

The present invention relates to processes and apparatuses for making phenol and cyclohexanone. In particular, the present invention relates to processes and apparatuses for making phenol and/or cyclohexanone by the cleavage of cyclohexylbenzene hydroperoxide in the presence of an acid catalyst. The present invention is useful, e.g., in producing phenol and cyclohexanone starting from hydroalkylation of benzene.

BACKGROUND

Phenol is an important product in the chemical industry and is useful in, for example, the production of phenolic resins, bisphenol A, ε-caprolactam, adipic acid, plasticizers, and polymers, such as nylon-6.

Currently, a common route for the production of phenol is the Hock process via cumene. This is a three-step process in which the first step involves alkylation of benzene with propylene in the presence of an acidic catalyst to produce cumene. The second step is oxidation, preferably aerobic oxidation, of cumene to the corresponding cumene hydroperoxide. The third step is the cleavage of the cumene hydroperoxide in the presence of heterogeneous or homogeneous catalysts into equimolar amounts of phenol and acetone, a co-product. However, the world demand for phenol is growing more rapidly than that for the acetone co-product. This imbalance depresses the value of the co-product reducing the economic benefits of the Hock process.

Thus, a process that co-produces higher ketones, rather than acetone, may be an attractive alternative route to the production of phenol. In addition, there is a growing market for cyclohexanone, which is used as an industrial solvent, as an activator in oxidation reactions and in the production of adipic acid, cyclohexanone resins, cyclohexanone oxime, caprolactam, and nylon-6.

As it has been recently disclosed, phenol and cyclohexanone can be co-produced by a novel process in which cyclohexylbenzene is oxidized to obtain cyclohexylbenzene hydroperoxide, which, in turn, is decomposed in the presence of an acid catalyst to the desired phenol and cyclohexanone in a cleavage process.

The chemistries in each step of the production of phenol and cyclohexanone from cyclohexylbenzene are very different from those of the Hock process for producing phenol and acetone from cumene.

For example, the cleavage reaction of cyclohexylbenzene hydroperoxide is more complex than the cleavage reaction of cumene hydroperoxide. More different side reactions may occur, significantly reducing the yield of phenol and/or cyclohexanone. Thus, novel cleavage process and equipment are desired for the cleavage reaction of cyclohexylbenzene hydroperoxide.

SUMMARY

The present disclosure provides a cleavage reactor and a process comprising a plurality of reaction zones connected in series. By configuring (i) each reaction zone other than the final reaction zone to comprise a fresh feed port for supplying fresh cyclohexylbenzene hydroperoxide, a processed feed port for receiving at least a portion of the effluent from a preceding reaction zone, (ii) the final reaction zone to comprise a fresh acid catalyst feed port and to recycle a portion of the effluent from the final effluent to the first reaction zone, and (iii) each reaction zone to comprise a heat exchanger downstream of the feed ports except the final reaction zone where the heat exchanger is optional, the cleavage reactor of the present disclosure can achieve a substantially uniform acid catalyst concentration in the reaction medium in each reaction zone other than the final reaction zone, a substantially uniform temperature in the reaction medium in each reaction zone, thereby avoiding undesirable side reactions and increasing the overall yield of phenol and cyclohexanone.

A first aspect of the present disclosure relates to a process for making phenol and/or cyclohexanone, the process comprising:

(A) providing a cleavage reactor having a plurality of reaction zones connected in series, the reaction zones comprising a first reaction zone, a final reaction zone and optionally one or more intermediate reaction zone(s) between the first reaction zone and the final reaction zone; wherein:

each of the reaction zones comprises a processed feed port, a fresh feed port, a heat exchanger at least partly downstream of the processed feed port and the fresh feed port in the same reaction zone, and an effluent port, except that the heat exchanger for the final reaction zone is optional;

the effluent port of any given reaction zone other than the final reaction zone is in fluid communication with the processed feed port of the immediately following reaction zone in the series; and the effluent port of the final reaction zone is in fluid communication with the processed feed port of the first reaction zone;

(B) supplying a fresh reaction feed comprising cyclohexylbenzene hydroperoxide to each reaction zone other than the final reaction zone via the fresh feed port of the reaction zone and producing an effluent at the effluent port of the reaction zone;

(C) supplying at least a portion of the effluent exiting the effluent port of each of the reaction zones other than the final reaction zone to the processed feed port of the immediately following reaction zone in the series;

(D) supplying an acid catalyst feed to the final reaction zone via the fresh feed port of the final reaction zone and producing a final effluent exiting the effluent port of the final reaction zone;

(E) recycling a portion of the final effluent to the first reaction zone via the processed feed port of the first reaction zone; and (F) obtaining phenol and/or cyclohexanone from a portion of the final effluent.

A second aspect of the present disclosure relates to cleavage reactor having a plurality of reaction zones connected in series, the reaction zones comprising a first reaction zone, a final reaction, and optionally one or more intermediate reaction zone(s) between the first reaction zone and the final reaction zone, wherein:

each of the reaction zones comprises a processed feed port, a fresh feed port, a heat exchanger at least partly downstream of the processed feed port and the fresh feed port in the same reaction zone, and an effluent port;

the effluent port of any given reaction zone other than the final reaction zone is in fluid communication with the processed feed port of the immediately following reaction zone in the series; and the effluent port of the final reaction zone is in fluid communication with the processed feed port of the first reaction zone;

the final reaction zone comprises an outlet downstream of the effluent port thereof for withdrawing a portion of the final effluent exiting the final reaction zone;

the fresh feed port of each of the reaction zone(s) except the final reaction zone is in fluid communication with a source of cyclohexylbenzene hydroperoxide; and the fresh feed port of the final reaction zone is in fluid communication with a source of an acid catalyst.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

BRIEF DESCRIPTION OF THE DRAWING

FIG. 1 is a schematic flow diagram of the cleavage reactor according to one embodiment of the present disclosure.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as listed, with or without overlapping with one or more other step, or in any other order, as the case may be. In addition, one or more, or even all steps, may be conducted simultaneously with regard to the same or different batch of material(s). For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two, or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a fractionation column.

As used herein, the generic term "dicylcohexylbenzene" ("DiCHB") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, diicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve used in the catalyst of the present disclosure is selected from (a) MCM-49; (b) MCM-56; and (c) isotypes of MCM-49 and MCM-56, such as ITQ-2.

The Cleavage Process and Equipment of the Present Disclosure

The cleavage of cyclohexyl-1-phenyl-1-hydroperoxide to make phenol and cyclohexanone involves the following Reaction-1:

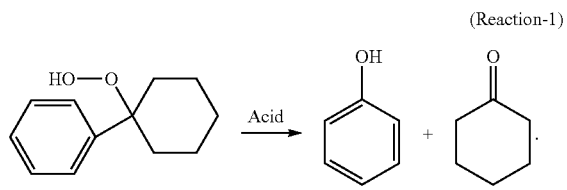

(Reaction-1)

This reaction is highly exothermic. A temperature increase in the reaction medium beyond the desirable range, even local and transient, can lead to many undesirable side reactions, which can decrease the yield of phenol and/or cyclohexanone significantly. Hence, there is a strong need to extract the heat generated in the reaction continuously from the reaction medium, and maintain a low and substantially uniform acid concentration in the reaction medium. The process and apparatus of the present disclosure achieves these and other goals.

The cleavage reactor used in the process of the present disclosure comprises multiple reaction zones including a first, final and optionally one or more intermediate reaction zone(s) connected in series such that at least a portion of the effluent exiting a given reaction zone at the effluent port thereof is supplied to a subsequent reaction zone at the processed feed port thereof. The reactor has a loop design in that a portion of the final effluent from the final reaction zone is recycled to the first reaction zone. It should be noted that however, it is possible that in the cleavage reactor of the present disclosure, in each reaction zone, there may be one or more vessels connected in parallel, wherein the cleavage reaction takes place. It should also be noted that it is possible that (i) the recycle stream from the final effluent of the final reaction zone is recycled only to the first reaction zone; or (ii) the recycle stream from the final effluent of the final reaction zone is recycled to both the first reaction zone and one or more intermediate reaction zone(s).

The reactor can take the shape of a vessel with or without stirring. In certain embodiments, the adjacent reaction zones can be connected via a conduit with or without intermediate equipment, such as heat exchanger, stirrer, pump, temperature sensor, and the like. In other embodiments, the adjacent reaction zones form an integrated reaction system, such that the effluent port of a preceding reaction zone may be the same as the processed feed port for the next reaction zone. Thus, the dividing line between two adjacent reaction zones may be arbitrary. Nonetheless, the apparatus and process are designed such that the desired cleavage reactions occur to various degrees in each of the reaction zones. Thus, as used herein, the term "in fluid communication" means that the two related zones have a relationship allowing the transportation of a fluid from one zone to the other. Thus, two zones in fluid communication with each other may be: (i) directly connected via a conduit such that a fluid can flow from one zone to the other without any manipulation, interruption or processing in the middle; or (ii) connected with each other via an intermediate component, such as a pump, a drum, a storage tank, a drying equipment, a heat exchanger, a chemical processing unit, and the like, such that a fluid exiting one zone is delivered to the other in the same physical and chemical state or in an altered state.

To each reaction zone other than the final reaction zone is fed two streams: (i) at least a portion of the effluent from the preceding reaction zone or the final reaction zone (in the case of the first reaction zone), considered as a processed feed with various concentrations of cyclohexylbenzene hydroperoxide, received by the processed feed port of the reaction zone; and (ii) a fresh reaction feed comprising cyclohexylbenzene hydroperoxide, received by the fresh feed port. Normally, the fresh feed port follows the processed feed port in a given reaction zone, so that fresh feed containing relatively high concentration of cyclohexylbenzene hydroperoxide can be diluted immediately by the exiting processed feed resulting in an overall low cyclohexylbenzene hydroperoxide concentration in the reaction zone. In desirable embodiments, all of the effluent exiting a given reaction zone other than the final reaction zone is fed into the next reaction zone via the processed feed port of the next reaction zone. In particularly advantageous embodiments, all of the acid catalyst present in the reaction media in the reaction zones other than the final reaction zone is carried over from the effluent existing the preceding reaction zone or the final reaction zone (in the case of the first reaction zone), and the only reaction zone where fresh acid catalyst feed is supplied is the final reaction zone. In this manner, the acid catalyst concentrations in the reaction medium in all reaction zones other than the final reaction zone are controlled uniform and no local spike can occur. Thus, even at the fresh feed port(s) where cyclohexylbenzene hydroperoxide concentration can be quite high, the cleavage reaction undergoes in a controlled fashion without generating an inordinately amount of heat because the overall acid catalyst concentration is low. The cleavage reactor and process are designed such that a great majority of the cyclohexylbenzene hydroperoxide entering into a given reaction zone would have been converted to phenol, cyclohexanone and by-products, if any, inside the same reaction zone, and thus the effluent exiting the reaction zone would advantageously have a low concentration of cyclohexylbenzene hydroperoxide.

To the final reaction zone is fed two streams: (i) at least a portion of the effluent exiting the reaction zone preceding the final reaction zone, which desirably comprise cyclohexylbenzene hydroperoxide at a low concentration, received by the processed feed port of the final reaction zone; and (ii) a stream of fresh acid catalyst feed, received by the fresh feed port of the final reaction zone. In particularly desirable embodiments, all of the cyclohexylbenzene hydroperoxide entering the final reaction zone is supplied from the effluent exiting the reaction zone preceding the final reaction zone, i.e., no fresh cyclohexylbenzene hydroperoxide is supplied to the final reaction zone, resulting in an overall low concentration of cyclohexylbenzene hydroperoxide throughout the reaction medium inside the final reaction zone. In embodiments where no fresh acid catalyst is supplied to any reaction zone other than the final reaction zone, among all reaction zones, the final reaction zone would have (a) the highest overall acid catalyst concentration; (b) the highest non-uniformity of the acid catalyst concentration because of the fresh introduction thereof; and (c) the lowest overall concentration of cyclohexylbenzene hydroperoxide. Because of the very low overall cyclohexylbenzene hydroperoxide concentration in the final reaction zone, the high overall and local acid catalyst concentration would not result in significant side reaction and by-products. In particularly desirable embodiments, the final reaction zone of the reactor is designed such that substantially all of the cyclohexylbenzene hydroperoxide is completely converted into phenol, cyclohexanone and by-products, if any, inside the final reactor, and the final effluent exiting the final reaction zone is thus substantially free of, e.g., cyclohexylbenzene hydroperoxide.

Every reaction zone is equipped with a heat exchanger for extracting the heat generated by the cleavage reaction, except for the final reaction zone where the heat exchanger can be optional. To that end, at least a part of the heat exchanger is downstream of the ports through which cyclohexylbenzene hydroperoxide is introduced. In desirable embodiments, the processed feed port and/or the fresh feed port are located inside the enclosure of a heat exchanger (i.e., once the processed feed and/or the fresh feed enters into the reaction zone, it is subjected to temperature management by the heat exchanger). Because the reaction medium circulating in the loop comprises the acid catalyst at various concentrations, the cyclohexylbenzene hydroperoxide fed into the reaction medium would undergo cleavage reaction generating heat. The downstream heat exchanger would serve to timely extract the heat so that the temperature of the reaction medium in each reaction zone is controlled within a desirable range.

The final effluent exiting the final reaction zone is partly recycled to the first reaction zone as processed feed to the first reaction zone, and partly withdrawn and processed in a next step to obtain the desired phenol and/or cyclohexanone. The final effluent may comprise, in additional to phenol, cyclohexanone: (i) a very low concentration of cyclohexylbenzene hydroperoxide; (ii) contaminants or solvent fed into the cleavage reactor from the fresh reaction feed(s) such as cyclohexylbenzene; (iii) the acid catalyst; and (iv) byproducts generated in the cleavage reactor. After neutralizing the acid, fractional distillation may be employed to separate phenol and/or cyclohexanone from the mixture.

Where there is one or more intermediate reaction zone(s) between the first and final reaction zones, the fresh reaction feeds fed into the reaction zones other than the final reaction zone may have the same or different composition(s). In general, the fresh feed fed into any of the reaction zones other than the final reaction zone may comprise: (i) cyclohexylbenzene hydroperoxide at a concentration in the range from a1 wt % to a2 wt %, where a1 can be 10, 15, 20, 25, 30, 35, 40, 45, 50, 55, 60, 65, 70, and 75, and a2 may be 90, 85, 80, 75, 70, 65, 60, 55, 50, 45, 40, 35, 30, 25, 20, as long as a1<a2; (ii) phenol at a concentration in the range from b1 wt % to b2 wt %, where b1 can be 0, 2, 4, 5, 6, 8, 10, 15, 20; and b2 can be 50, 45, 40, 35, 30, 25, 20, 15, as long as b1<b2; (iii) cyclohexanone at a concentration in the range from c1 wt % to c2 wt %, where c1 can be 0, 2, 4, 5, 6, 8, 10, 15, 20; and c2 can be 30, 28, 26, 25, 24, 22, 20, 18, 16, 15, as long as c1<c2; and (iv) cyclohexylbenzene at a concentration in the range from d1 wt % to d2%, where d1 can be 1, 2, 3, 4, 5, 6, 7, 8, 9, 10, 11, 12, 13, 14, 15, 20, 25, or 30, and d2 can be 50, 45, 40, 35, 30, 28, 26, 25, 24, 22, 20, 18, 16, 15, 14, 12, or 10, as long as d1<d2; where all of the percentages above are based on the total weight of the given fresh reaction feed supplied to the given reaction zone. Phenol may be intentionally included in the fresh feed stream due to the fact it is conducive to Reaction-1.

It is highly desirable that the final effluent exiting the final reaction zone has a low concentration of cyclohexylbenzene hydroperoxide. At the proper acid catalyst concentration and proper residence time, a great majority of cyclohexylbenzene hydroperoxide can be converted in the final reaction zone, especially in embodiments where all of the cyclohexylbenzene hydroperoxide in the reaction medium in the final reaction zone is supplied from the effluent from the reaction zone immediately preceding the final reaction zone. Thus, in desirable embodiments, the final effluent comprises cyclohexylbenzene hydroperoxide at a concentration of at most X ppm, based on the total weight of the final effluent, where X can be: 1000, 900, 800, 700, 600, 500, 400, 300, 200, 100, 90, 80, 70, 60, 50, 40, 30, 20, or even 10. In advantageous embodiments, the concentration of cyclohexylbenzene hydroperoxide in the final effluent is below the detection limit of regular gas chromatography equipment commercially available as of the filing date of the present application.

It is also highly desirable that a great majority of the cyclohexylbenzene hydroperoxide present in the reaction medium in any of the reaction zones is converted into products at the end of the reaction zone. This can be achieved at a relatively low acid catalyst concentration and relatively short residence time, owing to the high reaction rate of Reaction-1 at normal reaction temperatures. Thus, in desirable embodiments, the effluent exiting each reaction zone comprises cyclohexylbenzene hydroperoxide at a concentration of at most Y ppm, based on the total weight of the given effluent, where Y can be: 1000, 900, 800, 700, 600, 500, 400, 300, 200, 100, 90, 80, 70, 60, 50, 40, 30, 20, or even 10. In advantageous embodiments, the concentration of cyclohexylbenzene hydroperoxide in the effluent exiting each reaction zone is below the detection limit of regular gas chromatography equipment commercially available as of the filing date of the present application.

As a result of the high degree of conversion of the cyclohexylbenzene hydroperoxide in the reaction zones, the effluent exiting at least one of the reaction zones, such as the final reaction zone, the first reaction zone, or an intermediate reaction zone, if any, desirably the effluents exiting all of the reaction zones, may comprise phenol at a concentration in the range from A1 wt % to A2 wt %, based on the total weight of the given effluent, where A1 can be 10, 15, 20, 25, 30, 35, 40, 45, 50, 55, or 60, and A2 can be 80, 75, 70, 65, 60, 55, 50, 45, 40, 35, 30, 25, or 20, as long as A1<A2.

The effluent exiting at least one of the reaction zones, such as the final reaction zone, the first reaction zone, or an intermediate reaction zone, if any, desirably the effluents exiting all of the reaction zones, may comprise cyclohexanone at a concentration in the range from B1 wt % to B2 wt %, based on the total weight of the given effluent, where B1 can be 10, 15, 20, 25, 30, 35, 40, 45, or 48, and A2 can be 50, 45, 40, 35, 30, 25, or 20, as long as B1<B2.

It is highly desired that the same amount of phenol and cyclohexanone are produced from each mole of cyclohexylbenzene hydroperoxide in the reaction zone. However, depending on whether phenol and/or cyclohexanone is intentionally added into the reaction medium through the fresh reaction feed or other ports into the cleavage reactor, the molar ratio of phenol to cyclohexanone in the effluent exiting each reaction zone may vary from R1 to R2, where R1 can be 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, or 2.00, and R2 can be 8.00, 7.50, 7.00, 6.50, 6.00, 5.50, 5.00, 4.50, 4.00, 3.50, 3.00, 2.50, 2.40, 2.20, 2.00, 1.90, 1.80, 1.70, 1.60, 1.50, 1.40, 1.30, or 1.20, as long as R1<R2. Given the desirability of phenol in the reaction medium as described above, an advantageous range of the phenol to cyclohexanone molar ratio in one or more or all of effluents existing the reaction zones is from 0.95 to 1.50.

The cleavage reactor of the present disclosure may comprise merely two reaction zones: the first reaction zone to which fresh cyclohexylbenzene hydroperoxide is supplied, and the final reaction zone to which fresh acid catalyst is supplied. Alternatively, the cleavage reactor may comprise one or more intermediate reaction zone(s) between the first and final reaction zones. Depending on the desired capacity, the cleavage reactor may comprise, e.g., N1 to N2 reaction zones, where N1 can be 2, 3, 4, 5, 6, 7, 8, 9, 10, 15, 20, 25, 30, 35, 40, 45, or 50, and N2 can be 100, 95, 90, 85, 80, 75, 70, 65, 60, 55, 50, 45, 40, 35, 30, 25, or 20, as long as N1<N2. Better control of the temperatures can be achieved with more reaction zones at a given total capacity, given the larger number of heat exchangers available in the system and smaller amount of fresh cyclohexylbenzene hydroperoxide required to be processed at each given reaction zone. A particularly advantageous cleavage reactor comprises 5 to 20 reaction zones.

Desirably, in embodiments, the final reaction zone is a close approximation to a plug flow reactor. Desirably, all of the reaction zones are close approximations to a plug flow reactor.

The layout of the cleavage reactor enables precise control of the reaction medium temperature in each reaction zone, as mentioned above. Thus, the temperature of the reaction medium in all of the reaction zones can be advantageously controlled from T1° C. to T2° C., where T1 can be 5, 8, 10, 12, 15, 18, 20, 22, 24, 25, 26, 28, 30, 32, 34, 35, 36, 38, 40, 42, 44, 45, 48, or 50, and T2 can be 80, 75, 70, 68, 65, 64, 62, 60, 58, 56, 55, 54, 52, 50, 48, 46, 45, 44, 42, or 40, as long as T1<T2. A high degree of temperature uniformity can be achieved in each reactor as well. Thus, at any given time, the temperature variation at a given time in the reaction medium inside any given reaction zone can be controlled within ΔT ° C., where ΔT can be: 20, 18, 16, 15, 14, 12, 10, 9.0, 8.0, 7.0, 6.0, 5.0, 4.0, or even 3.0. The flow of the reaction medium inside the reactor can serve to mix the reaction medium, resulting in a high temperature uniformity and efficient heat extraction through the heat exchanger. However, it is also possible that mechanical mixing such as by static or moving stirrers may be used in one or more of the reaction zones or between the reaction zones as well. In desirable embodiments, the heat exchangers uses a stream of water having a temperature, e.g., in the range from 4° C. to 40° C., as a cooling medium. The temperature variation, ΔT, in a given reaction zone can be measured by placing a plurality of temperature sensors inside the reaction medium in the reaction zone, obtaining the measurement data at the given point of time, and calculating the ΔT according to ΔT=Tmax−Tmin, where Tmax is the highest measured temperature, and Tmin is the lowest measured temperature. One skilled in the art can determine the locations and number of temperature sensors in the reaction zone in order to obtain a statistically meaningful representation of the temperature distribution profile inside the reactor.

The recycle rate of the final effluent exiting the final reaction zone to the first reaction zone can vary. Thus, assuming in a given period time, the weight of the portion of the final effluent recycled to the first reaction zone is W1, and the total weight of the final effluent is W2, the recycle rate W1/W2 can be in a range from R1 to R2, where R1 can be 0.10, 0.15, 0.20, 0.25, 0.30, 0.35, 0.40, 0.45, or 0.50, and R2 can be 0.98, 0.96, 0.95, 0.94, 0.92, 0.90, 0.88, 0.86, 0.85, 0.84, 0.82, 0.80, 0.78, 0.75, 0.72, 0.70, 0.65, 0.60, 0.55, or 0.50, as long as R1<R2. At a high recycle rate W1/W2>0.50, the amount of each fresh reaction feed is small relative to the total amount of the reaction medium circulating in the reactor, resulting in relatively stable acid catalyst concentration in all of the reaction zones, which can be desirable in embodiments.

Advantageously, the heat exchangers in the respective reaction zones are separate from each other and are independently controlled, so that the temperature of each reaction zone can be separately monitored and adjusted where needed. However, it is not ruled out that one or more reaction zones may use different portions of a common heat exchanger. The feed ports of each reaction zone, including the fresh feed port and the processed feed port, may be located inside or outside of the enclosure of a heat exchanger of the reaction zone. At a minimum, at least part of a heat exchanger is located downstream of the feed ports in the reaction zone, so that heat generated by the cleavage reaction of fresh or existing cyclohexylbenzene hydroperoxide introduced into the reaction zone can be extracted and removed by the heat exchanger.

Residence time of the reaction medium in each reaction zone may vary. In the present disclosure, "residence time" of the reaction medium is represented by the reciprocal of the weight hourly space velocity of the reaction medium passing through the reaction zone. Thus, assuming in the final reaction zone, the residence time of the reaction medium is Tf; and in any reaction zone other than the final reaction zone, the residence time of the reaction medium is independently To, the ratio of Tf/To may be in the range from R1 to R2, where R1 can be 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0, and R2 can be 20, 18, 16, 15, 14, 12, 10, 8.0, 6.0, 5.0, 4.0, 3.0, 2.5, or 2.0, as long as R1<R2. It may be desirable that Tf/To>1.0, 1.5, 2.0, 2.5, or even 3.0, such that substantially all of the cyclohexylbenzene hydroperoxide is converted in the final reaction zone, resulting in an exceedingly low cyclohexylbenzene hydroperoxide concentration in the final effluent as described above.

In a particularly desirable, simple design of the cleavage reactor of the present disclosure, all of the reaction zones comprise a fluid path having the same cross-sectional area; the final reaction zone independently has a fluid path length Lf; each reaction zone other than the final reaction zone independently has a fluid path length Lo; and Lf/Lo is R1 to R2, where R1 can be 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0, and R2 can be 20, 18, 16, 15, 14, 12, 10, 8.0, 6.0, 5.0, 4.0, 3.0, 2.5, or 2.0, as long as R1<R2. As used herein, "a fluid path" is essentially the internal space of a reaction zone through which the reaction medium flows. "Fluid path length" is the length of the reaction zone in the general direction in which the reaction medium flows.

The acid catalyst used in the process of the present disclosure can be, e.g., sulfuric acid, sulfonic acid, p-toluene sulfonic acid, perchloric acid, hydrochloric acid, phosphoric acid, aluminum chloride, oleum, ferric chloride, boron trifluoride, sulfur dioxide, sulfur trioxide, other Bronsted or Lewis acid, and mixtures and combinations thereof. Sulfuric acid is particularly advantageous due to its low cost and availability. The acid catalyst feed supplied to the final reaction zone may comprise, e.g., (i) the acid at a concentration in the range from ca1 wt % to ca2 wt %, where ca1 can be 30, 40, 50, 60, 70, 80, 85, 88, 90, 92, 94, or 95, and ca2 can be 99, 98, 96, 95, 94, 92, 90, 88, 86, 85, 84, 82, 80, 75, 70, 65, 60, 55, or 50; (ii) water at a concentration in the range from cw1 wt % to cw2 wt %, where cw1 can be 0, 0.5, 1.0, 1.5, 2.0, 2.5, 3.0, 4.0, 5.0, 6.0, 8.0, 10, and cw2 can be 20, 18, 16, 15, 14, 12, 10, 8.0, 6.0, 5.5, 5.0, 4.5, or 4.0, and (iii) phenol at a concentration from cp1 wt % to cp2 wt %, where cp1 can be 0, 0.5, 1.0, 2.0, 3.0, 4.0, 5.0, 6.0, 8.0, 10, 12, 14, 15, 16, 18, 20, cp2 can be 50, 45, 40, 35, 30, 25, 20, 18, 16, 15, 12, or 10, as long as cp1<cp2, and all the percentages are based on the total weight of the acid catalyst feed.

Advantageously, to avoid excessive heat generation, reduce the corrosion of the equipment, desirably a relatively low concentration of the acid catalyst (such as sulfuric acid) is present in the reaction medium. Thus, in desirable embodiments, in the final effluent, the concentration of the acid is from C1 ppm to C2 ppm, based on the total weight of the final effluent, where C1 can be 1, 2, 3, 4, 5, 6, 8, 10, 15, 20, 25, 30, 35, 40, 45, 50, 55, 60, 65, 70, 75, 80, 85, 90, 95, or 100, and C2 can be 1000, 900, 800, 700, 600, 500, 450, 400, 350, 300, 250, 200, 150, 140, 120, 100, 95, 90, 85, 80, as long as C1<C2. In other desirable embodiments, in all of the effluents exiting all of the reaction zones, the concentration of the acid is from C1 ppm to C2 ppm, based on the total weight of the final effluent, where C1 can be 1, 2, 3, 4, 5, 6, 8, 10, 15, 20, 25, 30, 35, 40, 45, 50, 55, 60, 65, 70, 75, 80, 85, 90, 95, or 100, and C2 can be 1000, 900, 800, 700, 600, 500, 450, 400, 350, 300, 250, 200, 150, 140, 120, 100, 95, 90, 85, 80, as long as C1<C2. Desirably, the acid catalyst is fed into the final reaction zone only. However, it is not ruled out that the acid catalyst may be added into one or more of the other reaction zones.

In one particularly advantageous embodiment, the cyclohexylbenzene hydroperoxide used in the process of the present disclosure is produced by a process comprising the following steps:

(i) contacting benzene and hydrogen with a catalyst under hydroalkylation conditions to product a hydroalkylation effluent comprising cyclohexylbenzene; and (ii) oxidizing at least a portion of the cyclohexylbenzene to produce an oxidation effluent comprising cyclohexylbenzene hydroperoxide.

In other advantageous embodiments, step (F) of the process for making phenol and cyclohexanone according to the present disclosure comprises:

(Fa) neutralizing the portion of the final effluent to obtain a neutralized effluent; and (Fb) separating phenol and cyclohexanone from at least a portion of the neutralized effluent.

The final reaction zone of the cleavage reactor of the present disclosure also comprises an outlet downstream of the effluent port, through which a portion of the final effluent can be withdrawn as the cleavage reaction product stream, which will be processed in a subsequent stage, where it can be neutralized by a base, and then separated in one or more fractionation column(s), to obtain the final target product such as phenol and/or cyclohexanone.

Furthermore, in a desirable embodiment, the cleavage reactor comprises a pump between the final reaction zone and the first reaction zone adapted for pumping the recycled portion of the final effluent to the first reaction zone. Additional pumps may be installed between other reaction zones. These one or more pumps provide the energy required for the circulation of the reaction medium through the reactor system.

One or more the reaction zones may be equipped with a temperature sensor, concentration sensor, and the like, for monitoring the temperature, concentrations, and other process parameters therein. The temperature, concentration and other signals procured by the sensor(s) may be used to control and adjust at least one of the following: (a) the temperature, flow rate, concentration, and the like, of the fresh reaction feed(s) and the acid catalyst feed; (b) the temperature, flow rate, and the like, of one of more of the heat exchangers.

The present invention is particularly useful in making phenol and cyclohexanone starting from benzene hydroalkylation. The following is a detailed description of this embodiment.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

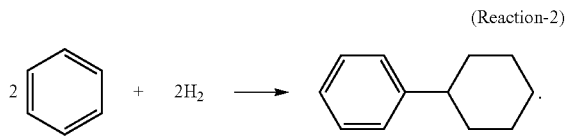 [SMILES: c1ccccc1 ; c1ccc(C2CCCCC2)cc1]
(Reaction-2)

Alternatively, cyclohexylbenzene can be produced by direct alkylation of benzene with cyclohexene in the presence of a solid-acid catalyst such as molecular sieves in the MCM-22 family according to the following Reaction-2:

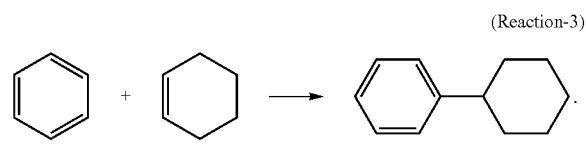 [SMILES: c1ccccc1 ; C1=CCCCC1 ; c1ccc(C2CCCCC2)cc1]
(Reaction-3)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 hr$^{-1}$ to 10 hr$^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added hydrogen, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

The cyclohexylbenzene feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

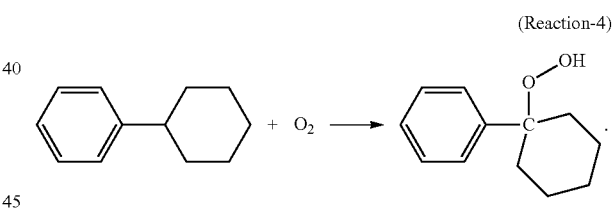

(Reaction-4)

In exemplary processes, the oxidizing step may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

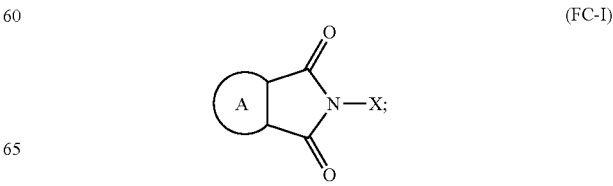

(FC-I)

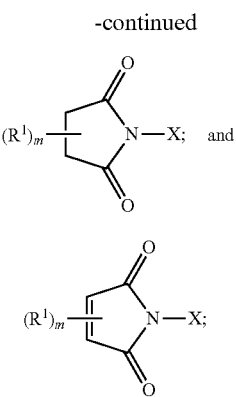

(FC-II)

(FC-III)

where:
A represents a ring optionally comprising a nitrogen, sulfur, or oxygen in the ring structure, and optionally substituted by an alkyl, an alkenyl, a halogen, or a N-, S-, or O-containing group or other group;
X represents a hydrogen, an oxygen free radical, a hydroxyl group, or a halogen;
$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and
m is 0, 1 or 2.

Examples of particularly suitable catalysts for the oxidation step include those represented by the following formula (FC-IV):

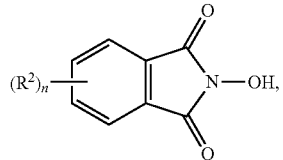

(FC-IV)

where:
$R^2$, the same or different at each occurrence, independently represents a halogen, a N-, S-, or O-containing group, or an optionally substituted linear or branched acyclic alkyl or cyclic alkyl group having 1 to 20 carbon atoms; and
n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from Cu1 wt % to Cu2 wt %, where Cu1 and Cu2 can be, independently, 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as Cu1<Cu2. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water. The concentration of water in the oxidation reaction product mixture exiting the oxidation reactor may range from C1a ppm to C1b ppm, based on the total weight of the oxidation reaction product mixture, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture portion, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently, 40, 45, 50, 55, 60, 65, 70, 75, 80, 85, 90, as long as Cc1<Cc2; and Cd1 and Cd2 can be, independently, 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently, 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently, 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

This step and the reactor for this step are described in detail above.

Separation and Purification

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

DESCRIPTION ACCORDING TO THE DRAWING

FIG. 1 schematically illustrates a cleavage reactor 101 comprising four reaction zones: a first reaction zone 103, a second reaction zone 105, a third reaction zone 107, and a fourth and final reaction zone 109. Fresh reaction feed 113 stream comprising cyclohexylbenzene hydroperoxide, supplied from storage 111, enters into the first reaction zone 103 via the first fresh reaction feed port 115, and combines with a recycle stream 147 comprising phenol, cyclohexanone and sulfuric acid, supplied from the final reaction zone 107. The recycle stream 147 enters the first reaction zone through a first processed feed port 145b upstream of port 115. The fresh cyclohexylbenzene hydroperoxide in stream 113, once in contact with the sulfuric acid supplied from stream 147, undergoes cleavage reaction, producing phenol, cyclohexanone and heat. A first heat exchanger 117, located downstream of port 115, extracts heat from the reaction medium by a cooling water stream, thereby maintaining the temperature of the reaction medium within the range from 20° C. to 80° C. The reaction medium exits the first reaction zone as a first effluent 118 at the first effluent port 118a. The first effluent 118 comprises phenol, cyclohexanone, and sulfuric acid. Desirably, the concentration of cyclohexylbenzene hydroperoxide in the first effluent 118 is below 100 ppm.

The full first effluent 118 then enters the second reaction zone 105 through the second processed feed port 118b. For the convenience of description, ports 118a and 118b are shown as separate ports in the FIGURE, although in practice they may be the same port in the system. A second fresh feed stream 119, also supplied from storage 111, enters the second reaction zone 105 at the second fresh feed port 121 and combines with stream 118. The fresh cyclohexylbenzene hydroperoxide in stream 119, once in contact with the sulfuric acid supplied from stream 118, undergoes cleavage reaction, producing phenol, cyclohexanone and heat. A second heat exchanger 123, located downstream of port 121, extracts heat from the reaction medium by a cooling water stream, thereby maintaining the temperature of the reaction medium within the range from 20° C. to 80° C. The reaction medium exits the second reaction zone as a second effluent 125 at the second effluent port 125a. The second effluent 125 comprises phenol, cyclohexanone, and sulfuric acid. Desirably, the concentration of cyclohexylbenzene hydroperoxide in the second effluent 118 is below 100 ppm.

The full second effluent 125 then enters the third reaction zone 107 through the third processed feed port 125b. For the convenience of description, ports 125a and 125b are shown as separate ports in the FIGURE, although in practice they may be the same port in the system. A third fresh feed stream 127, also supplied from storage 111, enters the third reaction zone 107 at the third fresh feed port 129 and combines with stream 125. The fresh cyclohexylbenzene hydroperoxide in stream 129, once in contact with the sulfuric acid supplied from stream 125, undergoes cleavage reaction, producing phenol, cyclohexanone and heat. A third heat exchanger 133, located downstream of port 129, extracts heat from the reaction medium by a cooling water stream, thereby maintaining the temperature of the reaction medium within the range from 20° C. to 80° C. The reaction medium exits the third reaction zone as a third effluent 135 at the third effluent port 135a. The third effluent 135 comprises phenol, cyclohexanone and sulfuric acid. Desirably, the concentration of cyclohexylbenzene hydroperoxide in the third effluent 135 is below 100 ppm.

The full third effluent 135 then enters the fourth and final reaction zone 109 through the fourth processed feed port 135b. For the convenience of description, ports 135a and 135b are shown as separate ports in the FIGURE, although in practice they may be the same port in the system. A fourth fresh feed stream 138 comprising sulfuric acid, supplied from storage 137, enters the fourth reaction zone 109 at the fourth fresh feed port 139 and combines with stream 135. The residual cyclohexylbenzene hydroperoxide, if any, in stream 135, undergoes further cleavage reaction in the presence of sulfuric acid supplied from streams 135 and 138, producing phenol, cyclohexanone and heat. A fourth heat exchanger 143, located downstream of port 139, extracts heat from the reaction medium by a cooling water stream, thereby maintaining the temperature of the reaction medium within the range from 20° C. to 80° C. A fourth effluent 145 at the fourth effluent port 145a is produced. The fourth effluent 145 comprises phenol, cyclohexanone and sulfuric acid. Desirably, the concentration of cyclohexylbenzene hydroperoxide in the fourth effluent 145 is below 100 ppm, or even below 80, 50, 40, 30, 20, or 10 ppm. The fourth effluent 145 is then divided into a recycle stream 147, which is recycled to the first reaction zone as described above, and a product stream 149, which is sent to the next stage, where phenol and cyclohexanone at acceptable purities can be separated and produced. Likewise, for the convenience of description, ports 145a and 145b are shown as separate ports in the FIGURE, although in practice they may be the same port in the system.

While the present invention has been described and illustrated by reference to particular embodiments, those of ordinary skill in the art will appreciate that the invention lends itself to variations not necessarily illustrated herein. For this reason then, reference should be made solely to the appended claims for purposes of determining the true scope of the present invention.

Non-limiting embodiments of the present disclosure include:

E1. A process for making phenol and/or cyclohexanone, the process comprising:

(A) providing a cleavage reactor having a plurality of reaction zones connected in series, the reaction zones comprising a first reaction zone, a final reaction zone and optionally one or more intermediate reaction zone(s) between the first reaction zone and the final reaction zone; wherein:

each of the reaction zones comprises a processed feed port, a fresh feed port, a heat exchanger at least partly downstream of the processed feed port and the fresh feed port in the same reaction zone, and an effluent port, except that the heat exchanger for the final reaction zone is optional;

the effluent port of any given reaction zone other than the final reaction zone is in fluid communication with the processed feed port of the immediately following reaction zone in the series; and the effluent port of the final reaction zone is in fluid communication with the processed feed port of the first reaction zone;

(B) supplying a fresh reaction feed comprising cyclohexylbenzene hydroperoxide to each reaction zone other than the final reaction zone via the fresh feed port of the reaction zone and producing an effluent at the effluent port of the reaction zone;

(C) supplying at least a portion of the effluent exiting the effluent port of each of the reaction zones other than the final reaction zone to the processed feed port of the immediately following reaction zone in the series;

(D) supplying an acid catalyst feed to the final reaction zone via the fresh feed port of the final reaction zone and producing a final effluent exiting the effluent port of the final reaction zone;

(E) recycling a portion of the final effluent to the first reaction zone via the processed feed port of the first reaction zone; and (F) obtaining phenol and/or cyclohexanone from a portion of the final effluent.

E1.5. The process of E1, wherein the final reaction zone comprises a final heat exchanger at least partly downstream of the processed feed port and the fresh feed port in the same reaction zone.

E2. The process of E1 or E1.5, wherein all of the acid catalyst present in all of the reaction zones other than the final reaction zone is supplied from the final effluent.

E3. The process of any of E1 to E2, wherein all of the cyclohexylbenzene hydroperoxide in the final reaction zone is supplied from the effluent from the reaction zone immediately preceding the final reaction zone.

E4. The process of E1, wherein in step (B), the fresh reaction feed comprises 10-90 wt % cyclohexylbenzene hydroperoxide, 0-30% phenol, 0-30% cyclohexanone, 0-40 wt % cyclohexylbenzene, all percentages based on the total weight of the fresh reaction feed.

E5. The process of any of E1 to E4, wherein the final effluent comprises at most 1000 ppm of cyclohexylbenzene hydroperoxide, in certain embodiments at most 800 ppm of cyclohexylbenzene hydroperoxide, in certain other embodiments at most 500 ppm of cyclohexylbenzene hydroperoxide.

E6. The process of any of E1 to E5, wherein in final effluent, the concentration of acid is from 5 to 1000 ppm based on the total weight of the final effluent.

E7. The process of any of E1 to E6, wherein in the effluent of each reaction zone other than the final reaction zone, the concentration of acid is from 1 ppm to 1000 ppm based on the total weight of the effluent of the reaction zone.

E8. The process of any of E1 to E7, wherein the effluent exiting the reaction zone immediately preceding the final reaction zone has a cyclohexylbenzene hydroperoxide concentration of from 1 to 1000 ppm based on the total weight of the effluent of the penultimate reactor.

E9. The process of any of E1 to E8, wherein in the effluent of each reaction zone other than the final reaction zone, the concentration of cyclohexylbenzene hydroperoxide is from 1 ppm to 500 ppm based on the total weight of the effluent of the reaction zone.

E10. The process of any of E1 to E9, wherein the effluent exiting the first reaction zone has a phenol concentration in a range from 10 wt % to 50 wt %, based on the total weight of the effluent exiting the first reaction zone.

E11. The process of any of E1 to E10, wherein the effluent exiting any given reaction zone other than the final reaction zone independently has a phenol concentration in a range from 10 wt % to 50 wt %, the percentages based on the total weight of the effluent exiting the given reaction zone.

E12. The process of any of E1 to E11, wherein the final effluent has a phenol concentration in a range from 10 wt % to 50 wt %, the percentages based on the total weight of the final effluent.

E13. The process of any of E1 to E12, wherein the effluent exiting the first reaction zone has a cyclohexanone concentration in a range from 10 wt % to 50 wt %, based on the total weight of the effluent exiting the first reaction zone.

E14. The process of any of E1 to E13, wherein the effluent exiting any given reaction zone other than the final reaction zone independently has a cyclohexanone concentration in a range from 10 wt % to 50 wt %, based on the total weight of the effluent exiting the given reaction zone.

E15. The process of any of E1 to E14, wherein the final effluent has a cyclohexanone concentration in a range from 10 wt % to 50 wt %, based on the total weight of the effluent exiting the final reaction zone and entering the first reaction zone.

E16. The process of any of E1 to E15, wherein the effluent exiting the first reaction zone has a phenol to cyclohexanone molar ratio in the range from 0.80 to 8.00.

E17. The process of any of E1 to E16, wherein the effluent exiting any given reaction zone other than the final reaction zone independently has a phenol to cyclohexanone molar ratio in the range from 0.80 to 8.00.

E18. The process of any of E1 to E17, wherein the final effluent has a phenol to cyclohexanone molar ratio in the range from 0.80 to 8.00.

E19. The process of any of E1 to E18, wherein the effluent exiting any given reaction zone independently has a phenol to cyclohexanone ratio in the range from 0.95 to 1.50.

E20. The process of any of E1 to E19, wherein the cleavage reactor comprises from 3 to 100 reaction zones.

E21. The process of E20, wherein the cleavage reactor comprises from 3 to 10 reaction zones.

E22. The process of any of E1 to E21, wherein the final reaction zone comprises a plug flow reactor.

E23. The process of any of E1 to E22, wherein the temperature of the reaction medium in the final reaction zone is controlled within a range from 15° C. to 80° C.

E24. The process of any of E1 to E23, wherein the temperature of the reaction medium in each reaction zone is controlled within a range from 15° C. to 80° C.

E25. The process of any of E1 to E24, where the temperature variation of the reaction medium at a given time in each reaction zone is $\Delta T$ ° C., where $\Delta T \leq 20$.

E26. The process of any of E1 to E25, wherein in a given period time, the weight of the portion of the final effluent recycled to the first reaction zone is W1, the total weight of the final effluent is W2, and W1/W2 is in a range from 0.10 to 0.98.

E27. The process of any of E1 to E26, wherein the composition of the fresh reaction feed supplied to each of the reaction zones other than the final reaction zone is the same.

E28. The process of any of E1 to E27, wherein the compositions of the fresh reaction feed supplied to all of the reaction zones other than the final reaction zone are not identical.

E29. The process of any of E1 to E28, wherein the heat exchangers in all of the reaction zones are separate and independent.

E30. The process of any of E1 to E29, wherein in at least one of the reaction zones, the fresh reaction feed port and/or the processed feed port are located inside the heat exchanger of the reaction zone.

E31. The process of any of E1 to E30, wherein:
in the final reaction zone, the residence time of the reaction medium is Tf;
in each reaction zone other than the final reaction zone, the residence time of the reaction medium is independently To; and
Tf/To is from 0.1 to 20.

E32. The process of any of E1 to E31, wherein:
all of the reaction zones comprise a fluid path having the same cross-sectional area;
the final reaction zone has a fluid path length Lf;
each reaction zone other than the final reaction zone independently has a fluid path length Lo; and
Lf/Lo is in a range from 0.1 to 20.

E33. The process of any of E1 to E32, wherein in each reaction zone other than the final reaction zone, the concentration of the acid in the reaction media is no higher than the concentration of the acid in the final effluent.

E34. The process of any of E1 to E33, wherein the acid catalyst feed comprises at least one of sulfuric acid, sulfonic acid, p-toluene sulfonic acid, perchloric acid, hydrochloric acid, phosphoric acid, aluminum chloride, oleum, ferric chloride, boron trifluoride, sulfur dioxide, and sulfur trioxide.

E35. The process of any of E1 to E34, wherein the acid catalyst feed comprises sulfuric acid.

E36. The process of E35, wherein the acid catalyst feed comprises sulfuric acid at a concentration of at least 90 wt %, based on the total weight of the acid catalyst feed.

E37. The process of E36, wherein the acid catalyst feed consists of sulfuric acid and water.

E38. The process of any of E34 to E37, wherein the acid catalyst feed further comprises phenol at a concentration of 1 wt % to 40 wt %, the percentage based on the total weight of the acid catalyst feed.

E39. The process of any of E1 to E38, wherein the heat exchangers cool the reaction medium in the reaction zones.

E40. The process of E39, wherein the heat exchangers use a stream of cooling water having a temperature in the range from 4° C. to 40° C., as a cooling medium.

E41. The process of any of E1 to E41, wherein the cyclohexylbenzene hydroperoxide is produced by a process comprising:
(i) contacting benzene and hydrogen with a catalyst under hydroalkylation conditions to produce a hydroalkylation effluent comprising cyclohexylbenzene; and
(ii) oxidizing at least a portion of the cyclohexylbenzene to produce an oxidation effluent comprising cyclohexylbenzene hydroperoxide.

E42. A cleavage reactor having a plurality of reaction zones connected in series, the reaction zones comprising a first reaction zone, a final reaction, and optionally one or more intermediate reaction zone(s) between the first reaction zone and the final reaction zone, wherein:
each of the reaction zones comprises a processed feed port, a fresh feed port, a heat exchanger at least partly downstream of the processed feed port and the fresh feed port in the same reaction zone, and an effluent port;
the effluent port of any given reaction zone other than the final reaction zone is in fluid communication with the processed feed port of the immediately following reaction zone in the series; and
the effluent port of the final reaction zone is in fluid communication with the processed feed port of the first reaction zone;
the final reaction zone comprises an outlet downstream of the effluent port thereof for withdrawing a portion of the final effluent exiting the final reaction zone;

the fresh feed port of each of the reaction zone(s) except the final reaction zone is in fluid communication with a source of cyclohexylbenzene hydroperoxide; and the fresh feed port of the final reaction zone is in fluid communication with a source of an acid catalyst.

E43. The cleavage reactor of E42 comprising at least three reaction zones in total.

E44. The cleavage reactor of E42, comprising from 3 to 50 reaction zones in total.

E45. The cleavage reactor of any of E42 to E44, wherein:
all of the reaction zones comprise a fluid path having the same cross-sectional area;
the final reaction zone has a fluid path length Lf;
each reaction zone other than the final reaction zone independently has a fluid path length Lo; and
Lf/Lo is in a range from 0.1 to 20.

E46. The cleavage reactor of any of E42 to E45, wherein the heat exchanger(s) uses water as a cooling medium.

E47. The cleavage reactor of any of E42 to E46, further comprising at least one pump located between the effluent port of the final reaction zone and the processed feed port of the first reaction zone adapted for supplying at least a portion of the final effluent exiting the final reaction zone to the first reaction zone.

E48. The cleavage reactor of any of E42 to E47, further comprising a temperature sensor located in at least one of the reaction zones for monitoring the temperature of the reaction medium therein.

E49. The cleavage reactor of E48, wherein the temperature from the signal temperature sensor is used to control at least one of:
the feed rate of at least one of the fresh reaction feed and the acid catalyst feed; and
the cooling power provided by at least one of the heat exchanger(s).

E50. The cleavage reactor of any of E42 to E49, further comprising a controlling device controlling the amount W1, of the portion of the final effluent exiting the final reaction zone recycled to the first reaction zone, such that $0.10 \leq W1/W2 \leq 0.95$, wherein W2 is the total amount of the final effluent.

The invention claimed is:

1. A process for making phenol and/or cyclohexanone, the process comprising:
    (A) providing a cleavage reactor having a plurality of reaction zones connected in series, the reaction zones comprising a first reaction zone, a final reaction zone and optionally one or more intermediate reaction zone(s) between the first reaction zone and the final reaction zone; wherein:
    each of the reaction zones comprises a processed feed port, a fresh feed port, a heat exchanger at least partly downstream of the processed feed port and the fresh feed port in the same reaction zone, and an effluent port, except that the heat exchanger for the final reaction zone is optional;
    the effluent port of any given reaction zone other than the final reaction zone is in fluid communication with the processed feed port of the immediately following reaction zone in the series; and
    the effluent port of the final reaction zone is in fluid communication with the processed feed port of the first reaction zone;
    (B) supplying a fresh reaction feed comprising cyclohexylbenzene hydroperoxide to each reaction zone other than the final reaction zone via the fresh feed port of the reaction zone and producing an effluent at the effluent port of the reaction zone;
    (C) supplying at least a portion of the effluent exiting the effluent port of each of the reaction zones other than the final reaction zone to the processed feed port of the immediately following reaction zone in the series;
    (D) supplying an acid catalyst feed to the final reaction zone via the fresh feed port of the final reaction zone and producing a final effluent exiting the effluent port of the final reaction zone;
    (E) recycling a portion of the final effluent to the first reaction zone via the processed feed port of the first reaction zone; and
    (F) obtaining phenol and/or cyclohexanone from a portion of the final effluent.

2. The process of claim 1, wherein all of the acid catalyst present in all of the reaction zones other than the final reaction zone is supplied from the final effluent.

3. The process of claim 1, wherein all of the cyclohexylbenzene hydroperoxide in the final reaction zone is supplied from the effluent from the reaction zone immediately preceding the final reaction zone.

4. The process of claim 1, wherein the final reaction zone comprises a final heat exchanger at least partly downstream of the processed feed port and the fresh feed port in the same reaction zone.

5. The process of claim 1, wherein in step (B), the fresh reaction feed comprises 10-90 wt % cyclohexylbenzene hydroperoxide, 0-30% phenol, 0-30% cyclohexanone, and 0-40 wt % cyclohexylbenzene, all percentages being based on the total weight of the fresh reaction feed.

6. The process of claim 1, wherein the final effluent comprises at most 1000 ppm of cyclohexylbenzene hydroperoxide.

7. The process of claim 1, wherein in the effluent exiting any given reaction zones, the concentration of the acid catalyst is from 5 to 1000 ppm based on the total weight of the effluent of the given reaction zone.

8. The process of claim 1, wherein the effluent exiting any given reaction zone independently has a phenol concentration in the range from 10 wt % to 50 wt % and a cyclohexanone concentration in the range from 10 wt % to 50 wt %, the percentages being based on the total weight of the effluent exiting the given reaction zone.

9. The process of claim 1, wherein the effluent exiting the reaction zone immediately preceding the final reaction zone has a cyclohexylbenzene hydroperoxide concentration of from 1 to 1000 ppm, based on the total weight of the effluent of the reaction zone.

10. The process of claim 1, wherein the final effluent has a cyclohexylbenzene hydroperoxide concentration in the range from 1 to 100 ppm, based on the total weight of the effluent exiting the given reaction zone.

11. The process of claim 1, wherein the effluent exiting any given reaction zone independently has a phenol to cyclohexanone molar ratio in the range from 0.80 to 8.00.

12. The process of claim 1, wherein the cleavage reactor comprises from 3 to 50 reaction zones.

13. The process of claim 1, wherein the temperature of the reaction medium in any given reaction zone is controlled within the range from 15° C. to 80° C.

14. The process of claim 1, wherein the temperature variation of the reaction medium at a given point of time in any given reaction zone is $\Delta T$ ° C., where $\Delta T \leq 20$.

15. The process of claim 1, wherein in a given period time, the weight of the portion of the final effluent recycled to the first reaction zone is W1, the total weight of the final effluent is W2, and W1/W2 is in a range from 0.10 to 0.98.

16. The process of claim 1, wherein:
in the final reaction zone, the residence time of the reaction medium is Tf;
in each reaction zone other than the final reaction zone, the residence time of the reaction medium is independently To; and
Tf/To is from 0.1 to 20.

17. The process of claim 1, wherein the acid catalyst feed comprises at least one of sulfuric acid, sulfonic acid, p-toluene sulfonic acid, perchloric acid, hydrochloric acid, phosphoric acid, aluminum chloride, oleum, ferric chloride, boron trifluoride, sulfur dioxide, and sulfur trioxide.

18. The process of claim 1, wherein the acid catalyst feed comprises sulfuric acid at a concentration of at least 90 wt %, based on the total weight of the acid catalyst feed.

19. The process of claim 1, wherein the acid catalyst feed further comprises phenol at a concentration of 1 wt % to 40 wt %, the percentage based on the total weight of the acid catalyst feed.

20. The process of claim 1, wherein the cyclohexylbenzene hydroperoxide is produced by a process comprising:
(i) contacting benzene and hydrogen with a catalyst under hydroalkylation conditions to produce a hydroalkylation effluent comprising cyclohexylbenzene; and
(ii) oxidizing at least a portion of the cyclohexylbenzene to produce an oxidation effluent comprising cyclohexylbenzene hydroperoxide.

21. A cleavage reactor having a plurality of reaction zones connected in series, the reaction zones comprising a first reaction zone, a final reaction, and optionally one or more intermediate reaction zone(s) between the first reaction zone and the final reaction zone, wherein:
each of the reaction zones comprises a processed feed port, a fresh feed port, a heat exchanger at least partly downstream of the processed feed port and the fresh feed port in the same reaction zone, and an effluent port;
the effluent port of any given reaction zone other than the final reaction zone is in fluid communication with the processed feed port of the immediately following reaction zone in the series;
the effluent port of the final reaction zone is in fluid communication with the processed feed port of the first reaction zone;
the final reaction zone comprises an outlet downstream of the effluent port thereof for withdrawing a portion of the final effluent exiting the final reaction zone;
the fresh feed port of each of the reaction zone(s) except the final reaction zone is in fluid communication with a source of cyclohexylbenzene hydroperoxide; and
the fresh feed port of the final reaction zone is in fluid communication with a source of an acid catalyst.

22. The cleavage reactor of claim 21 comprising from 3 to 50 reaction zones in total.

23. The cleavage reactor of claim 21, wherein:
all of the reaction zones comprise a fluid path having the same cross-sectional area;
the final reaction zone has a fluid path length Lf;
each reaction zone other than the final reaction zone independently has a fluid path length Lo; and
Lf/Lo is in a range from 0.1 to 20.

24. The cleavage reactor of claim 21, wherein the heat exchanger(s) uses water as a cooling medium.

25. The cleavage reactor of claim 21, further comprising at least one pump located between the effluent port of the final reaction zone and the processed feed port of the first reaction zone adapted for supplying at least a portion of the final effluent exiting the final reaction zone to the first reaction zone.

* * * * *